United States Patent [19]

Huang et al.

[11] Patent Number: 4,857,664
[45] Date of Patent: Aug. 15, 1989

[54] PROCESS FOR THE PRODUCTION OF ETHER AND ALCOHOL

[75] Inventors: Tracy J. Huang, Lawrenceville; Rene B. LaPierre, Medford; Samuel A. Tabak, Wenonah, all of N.J.

[73] Assignee: Mobil Oil Corporation, New York, N.Y.

[21] Appl. No.: 265,324

[22] Filed: Oct. 27, 1988

Related U.S. Application Data

[63] Continuation of Ser. No. 139,543, Dec. 30, 1987, abandoned.

[51] Int. Cl.$^4$ .................... C07C 41/06; C07C 41/09; C07C 41/01
[52] U.S. Cl. .................... 568/695; 568/697; 568/698; 568/699
[58] Field of Search ............... 568/694, 695, 697, 699, 568/698

[56] References Cited

U.S. PATENT DOCUMENTS

| | | |
|---|---|---|
| 2,162,913 | 6/1939 | Eversole et al. . |
| 2,477,380 | 7/1949 | Kreps et al. . |
| 2,797,247 | 6/1957 | Munster . |
| 2,798,097 | 7/1957 | Hettinger, Jr. et al. . |
| 2,805,260 | 9/1957 | Keith . |
| 2,830,090 | 4/1958 | Teter et al. . |
| 2,861,045 | 11/1958 | Langer, Jr. . |
| 2,891,999 | 6/1959 | Langer, Jr. . |
| 3,006,970 | 10/1961 | Beuther et al. . |
| 3,198,752 | 8/1965 | Bridger et al. . |
| 3,810,849 | 5/1974 | Massie . |
| 3,989,762 | 11/1976 | Ester . |
| 4,042,633 | 8/1977 | Woods . |
| 4,175,210 | 11/1979 | Selwitz et al. . |
| 4,182,914 | 1/1980 | Imaizumi . |
| 4,214,107 | 7/1980 | Chang et al. . |
| 4,334,890 | 6/1982 | Kochar et al. . |
| 4,418,219 | 11/1983 | Hanes et al. . |
| 4,499,313 | 2/1985 | Okumura et al. . |
| 4,605,787 | 8/1986 | Chu et al. . |

FOREIGN PATENT DOCUMENTS

| | | |
|---|---|---|
| 0055045 | 6/1982 | European Pat. Off. . |
| 0210793 | 2/1987 | European Pat. Off. . |
| 133661 | 1/1979 | Fed. Rep. of Germany . |
| 25345 | 2/1984 | Japan . |

Primary Examiner—Howard T. Mars
Attorney, Agent, or Firm—Alexander J. McKillop; Charles J. Speciale; Malcolm D. Keen

[57] ABSTRACT

Olefin undergoes conversion in the presence of water to a mixture of alcohol and ether which is then subjected to various downstream operations including distillation and decantation to provide an ether-rich product containing little if any water. If desired the ether can be combined in any predetermined ratio with co-produced alcohol to provide alcohol/ether mixtures of desired composition. The foregoing process is especially suitable to the conversion of propylene and propylene-containing streams to diisopropyl ether and mixtures of isopropyl alcohol and diisopropyl ether which are useful, inter alia, as octane improves for gasoline.

13 Claims, 1 Drawing Sheet

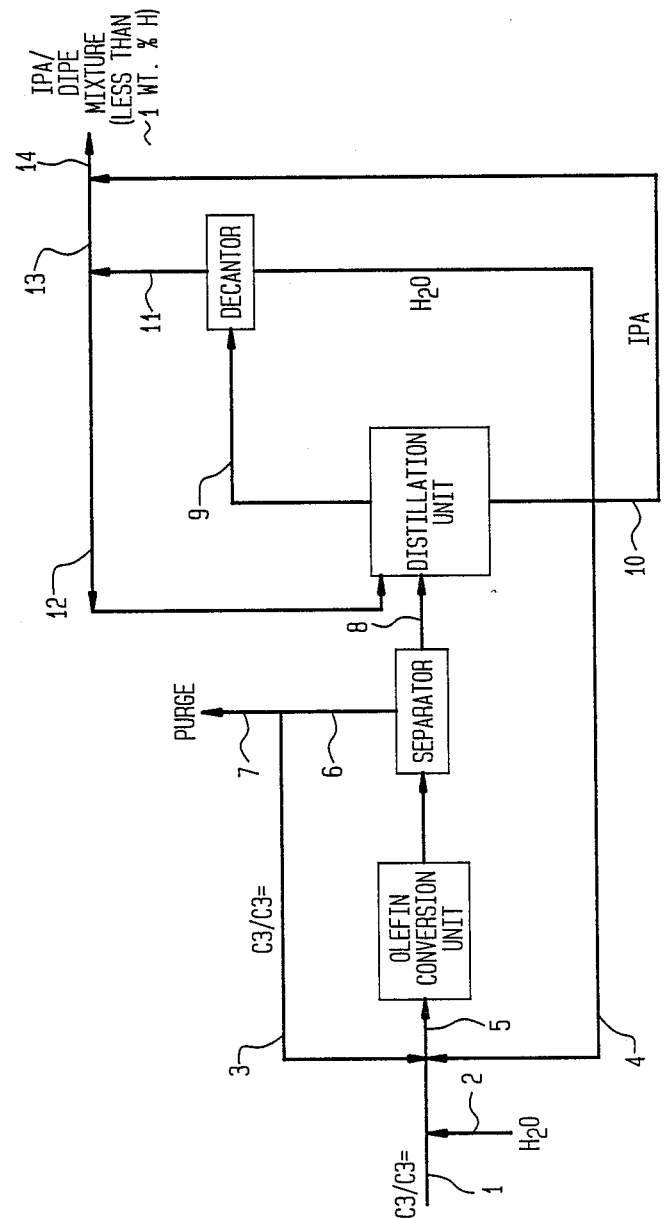

PROCESS FOR THE PRODUCTION OF ETHER AND ALCOHOL

CROSS REFERENCE TO RELATED APPLICATIONS

This is a continuation of copending application Ser. No. 139,543, filed on Dec. 30, 1987 abandoned.

This application is related to commonly assigned, concurrently filed U.S. patent application Ser. Nos. (139,570, 139,567 and 139,566) which are concerned with the production of alcohol(s) and/or ether(s).

BACKGROUND OF THE INVENTION

This invention relates to a process for the production of ether(s) and, optionally, mixtures of alcohol(s) and ether(s) of predetermined composition. More particularly, the invention relates to a process for the conversion of a light olefin such as ethylene, propylene, butenes, pentenes, hexenes, heptenes, etc., and their mixtures, in a conversion unit employing an acidic zeolite as olefin conversion catalyst to produce a mixture of alcohol(s) and ether(s) and thereafter recovering the ether(s) containing at most only small amounts of water. If desired, the ether(s) can be recombined with co-produced alcohol(s) to provide substantially dry alcohol/ether mixtures in virtually any desired ratio. The ether(s) and their mixtures with alcohol(s) are useful, inter alia, as high octane blending stocks for gasoline.

There is a need for an efficient catalytic process for manufacturing ethers and alcohols from light olefins thereby augmenting the supply of high octane blending stocks for gasoline. Lower molecular weight ethers such as diisopropyl ether (DIPE) and alcohols such as isopropyl alcohol (IPA) are in the gasoline boiling range and are known to have a high blending octane number. In addition, by-product propylene from which DIPE and IPA can be made is usually available in a fuels refinery. The petrochemicals industry also produces mixtures of light olefin streams in the $C_2$ to $C_7$ molecular weight range and the conversion of such streams or fractions thereof to ethers and alcohols can also provide products which are useful as solvents and as blending stocks for gasoline.

The catalytic hydration of olefins to provide alcohols and ethers is a well-established art and is of significant commercial importance. Representative olefin hydration processes are disclosed in U.S. Pat. Nos. 2,162,913; 2,477,380; 2,797,247; 3,798,097; 2,805,260; 2,830,090; 2,861,045; 2,891,999; 3,006,970; 3,198,752; 3,810,849; and, 3,989,762, among others.

Olefin hydration employing zeolite catalysts is known. As disclosed in U.S. Pat. No. 4,214,107, lower olefins, in particular, propylene, are catalytically hydrated over a crystalline aluminosilicate zeolite catalyst having a silica to alumina ratio of at least 12 and a Constraint Index of from 1 to 12, e.g., HZSM-5 type zeolite, to provide the corresponding alcohol, essentially free of ether and hydrocarbon by-product.

According to U.S. Pat. No. 4,499,313, an olefin is hydrated to the corresponding alcohol in the presence of hydrogen-type mordenite or hydrogen-type zeolite Y, each having a silica-alumina molar ratio of 20 to 500. The use of such a catalyst is said to result in higher yields of alcohol than olefin hydration processes which employ conventional solid acid catalysts. Use of the catalyst is also said to offer the advantage over ion-exchange type olefin hydration catalysts of not being restricted by the hydration temperature. Reaction conditions employed in the process include a temperature of from 50°–300° C., preferably 100°–250° C., a pressure of 5 to 200 kg/cm² to maintain liquid phase or gas-liquid multi-phase conditions and a mole ratio of water to olefin of from 1 to 20. The reaction time can be 20 minutes to 20 hours when operating batchwise and the liquid hourly space velocity (LHSV) is usually 0.1 to 10 in the case of continuous operation.

European Patent Application 210,793 describes an olefin hydration process employing a medium pore zeolite as hydration catalyst. Specific catalysts mentioned are Theta-1, said to be preferred, ferrierite, ZSM-22, ZSM-23 and NU-10.

The reaction of light olefins with alcohols to provide ethers is also a well known type of process. According to U.S. Pat. No. 4,042,633, DIPE is prepared from isopropyl alcohol (IPA) employing montmorillonite clay catalysts, optionally in the presence of added propylene. U.S. Pat. No. 4,175,210 discloses the use of silicatungstic acid as catalyst for the reaction of olefin(s) with alcohol to provide ether(s). As disclosed in U.S. Pat. No. 4,182,914, DIPE is produced from IPA and propylene in a series of operations employing a strongly acidic cation exchange resin as catalyst. In the process for producing a gasoline blending stock described in U.S. Pat. No. 4,334,890, a mixed $C_4$ stream containing isobutylene is reacted with aqueous ethanol to form a mixture of ethyl tertiary butyl ether and tertiary butanol. U.S. Pat No. 4,418,219 describes the preparation of methyl tertiary-butyl ether (MTBE), a high octane blending agent for motor fuels, by reacting isobutylene and methanol in the presence of, as catalyst, boron phosphate, blue tungsten oxide or a crystalline aluminosilicate zeolite having a silica to alumina mole ratio of at least 12:1 and a Constraint Index of from 1 to about 12 as catalyst. U.S. Pat. No. 4,605,787 discloses the preparation of alkyl tert-alkyl ethers such as MTBE and methyl tert-amyl ether (MTAE) by the reaction of a primary alcohol with an olefin having a double bond on a tertiary carbon atom employing as catalyst an acidic zeolite having a constraint index of from about 1 to 12, e.g., zeolite ZSM-5, 11, 12, 23 dealuminized zeolite Y and rare earth exchanged zeolite Y. European Patent Application 55,045 describes a process for reacting an olefin and an alcohol to provide an ether, e.g., isobutene and methanol to provide MTBE, in the presence of an acidic zeolite such as zeolite Beta, zeolites ZSM-5, 8, 11, 12, 23, 35, 43 and 48 and others, as catalyst. Germany Patent No. 133,661 describes the reaction of isobutene and methanol to provide a mixture of products including MTBE, butanol and isobutene dimer in the presence of acidic zeolite Y as catalyst. According to Japan Patent No. 59-25345, a primary alcohol is reacted with a tertiary olefin in the presence of a zeolite having a silica to alumina mole ratio of at least 10 and the x-ray diffraction disclosed therein to provide a tertiary ether.

It is an object of the present invention to provide a process for converting low cost, readily available sources of light olefins to ether(s) and, optionally, mixtures of alcohol(s) and ether(s), which can be used as high octane blending stocks for gasoline.

It is another object of the invention to provide a process for catalytically converting olefin(s) in an olefin conversion unit to mixtures of alcohol(s) and ether(s) employing an acidic zeolite catalyst and thereafter recovering the ether(s) in essentially pure form.

It is a specific object of this invention to react a feed containing a substantial amount of propylene with water in an olefin conversion unit in the presence of an acidic large pore zeolite such as zeolite Beta to provide a mixture of IPA and DIPE and to recover the DIPE in pure form or to add co-produced substantially dry IPA to said DIPE in a predetermined ratio.

SUMMARY OF THE INVENTION

By way of realizing the foregoing and other objects of the invention, a process is provided for producing ether containing at most relatively minor amounts of water which comprises:

(a) contacting at least one light olefin with water in an olefin conversion unit in the presence of an acidic zeolite as catalyst to provide an aqueous mixture of alcohol and ether, the olefin conversion unit being operated under conditions which are effective to provide alcohol by the reaction of olefin and water therein and ether by the dehydration of alcohol and/or by the reaction of olefin and alcohol therein;

(b) introducing the aqueous mixture of alcohol and ether into a distillation unit supplied with at least a part of the ether layer recovered from a downstream decantation operation, said distillation unit being operated under conditions which are effective to provide an azeotropic overheads fraction comprising ether, water, oligomer and minor amounts of alcohol, and a bottoms fraction comprising a major amount of alcohol and a minor amount of ether alcohol;

(c) introducing the azeotropic overheads fraction into a decanter unit operated under conditions which are effective to provide a ether layer containing at most negligible amounts of water and an aqueous layer containing negligible amounts of alcohol; and, (d) introducing at least part of the ether layer into the distillation unit to reduce the water content of the final ether product.

The present process offers great flexibility in providing essentially pure ethers or ethers combined with controlled quantities of alcohols.

BRIEF DESCRIPTION OF THE DRAWINGS

The annexed figure of drawing is a schematic representation of the process of the invention as applied to the production of an IPA/DIPE mixture of predetermined composition containing less than 1 weight percent water.

DESCRIPTION OF THE PREFERRED EMBODIMENTS

The present invention is applicable to the conversion of individual light olefins and mixtures of olefins of various structures, preferably within the $C_{2-7}$ range, to ethers. Accordingly, the invention is applicable to the conversion of ethylene, propylene, butenes, pentenes, hexenes and heptenes, mixtures of these and other olefins such as gas plant off-gas containing ethylene and propylene, naphtha cracker off-gas containing light olefins, fluidized catalytic cracked (FCC) light gasoline containing pentenes, hexenes and heptenes, refinery FCC propane/propylene streams, etc. For example, a typical FCC light olefin stream possesses the following composition:

| Typical Refinery FCC Light Olefin Composition | | |
|---|---|---|
| | Wt. % | Mole % |
| Ethane | 3.3 | 5.1 |
| Ethylene | 0.7 | 1.2 |
| Propane | 14.5 | 15.3 |
| Propylene | 42.5 | 46.8 |
| Isobutane | 12.9 | 10.3 |
| n-Butane | 3.3 | 2.6 |
| Butenes | 22.1 | 18.3 |
| Pentanes | 0.7 | 0.4 |

The process of the invention is especially applicable to the conversion of propylene and propylene-containing streams to DIPE and IPA/DIPE mixtures containing little if any water.

The conversion of the light olefin takes place in an olefin conversion unit wherein several reactions occur simultaneously to provide a mixture of alcohol and ether. Thus, olefin will react with water to produce alcohol, alcohol will react with olefin to produce ether and/or alcohol will undergo dehydration to produce ether.

The foregoing olefin conversion reactions can be carried out under liquid phase, vapor phase or mixed vapor-liquid phase conditions in batch or in a continuous manner under stirred tank reactor or fixed bed flow reactor conditions, e.g., trickle-bed, liquid-up-flow, liquid-down-flow, counter-current flow, co-current flow, etc.

In general, the useful olefin conversion catalysts embrace two categories of zeolite, namely, the intermediate pore size variety as represented, for example, by ZSM-5, which possess a Constraint Index of greater than about 2 and the large pore variety as represented, for example, by zeolites Y and Beta, which possess a Constraint Index no greater than about 2. Both varieties of zeolites will possess a framework silica-to-alumina ratio of greater than about 7, usually greater than at least about 20, preferably greater than at least about 200 and more preferably still, greater than about 500. The zeolite will be in the acid form and as such, will possess an alpha value of at least about 1, preferably at least about 10 and more preferably at least about 100. It will often be advantageous to provide the zeolite as a composite bound with catalytically active or inactive material such as alumina or silica which is stable under the olefin conversion conditions employed.

Of particular interest for use herein are the large pore acidic zeolites, e.g., zeolite Beta, X, L, Y, USY, REY, Deal Y, ZSM-3, ZSM-4, ZSM-12, ZSM-20 and ZSM-50, as disclosed in commonly assigned, concurrently filed U.S. patent application Ser. No. 139,567. In accordance with said application, these large pore zeolite catalysts are used to effect the conversion of light olefin(s) to a mixture of alcohol(s) and ether(s) by contacting the olefin(s) with water in the vapor and/or liquid phase at a temperature of from about 100° to 230° C., preferably from about 120° to about 220° C. and most preferably from about 140° to about 200° C., a total system pressure of at least about 5 atm, preferably at least about 20 atm and more preferably at least about 40 atm, a water to total olefin mole ratio of from 0.1 to less than about 1.0, preferably from about 0.2 to 0.8 and most preferably from about 0.3 to 0.7 and an LHSV of from about 0.1 to about 10 in the presence of an acidic form of the zeolite. In the specific case of acidic zeolite Beta, and as described in commonly assigned, concurrently filed U.S. patent application Serial No. 139,570, the contents of which are incorporated herein, the hydration conditions need not be so limited as those stated above for the case of large pore zeolites generally. Thus, use of acidic zeolite Beta can be accompanied by essentially any practical set of hydration conditions which provides alcohol(s) and ether(s) in appreciable amounts. As disclosed in said application, good results can generally be obtained employing a temperature ranging from ambient up to about 300° C., preferably from about 50° to about 220° C. and more preferably from about 90° to about 200° C., a total system pressure of at least about 5 atm, preferably at least about 20 atm and more preferably at least abut 40 atm, a water to total olefin mole ratio of from about 1 to about 30, preferably from about 0.2 to about 15 and most preferably from about 0.3 to about 5, and an LHSV of from about 0.1 to about 10. It may be noted that at the unusually low water:olefin mole ratios called for by the process disclosed in U.S patent application Ser. No. 139,567, the production of olefin hydration products employing Following condensation of the azeotrope from the distillation tower, the liquid product is introduced into a decanter unit where phase separation takes place. The decanter overheads are recovered as essentially dry ether and the aqueous decanter bottoms containing a small amount of alcohol can, if desired, be introduced into the olefin conversion unit.

The following example is illustrative of the process of the invention.

EXAMPLE 1

The conversion of propylene contained in a propylene/propane propane refinery stream (70 mole % propylene, 30 mole % propane) is illustrated in the process scheme shown in the appended FIGURE of drawing. The conditions of the propylene conversion employing an extrudate of zeolite Beta (85 wt. %) bound with silica (15 wt %) are: 160° C., 1800 psig, 0.5 water to propylene mole ratio and 0.5 weight hourly space velocity (WHSV) based on propylene. The results in moles/hr of feeds/products are set forth in the following Table:

TABLE

| Feed/Product Stream | IPA/DIPE Via Propylene Conversion over Zeolite Beta Moles/Hr | | | | | | | | | | | | | | |
|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | Wt % |
| Propane | 155.0 | — | 157.9 | — | 312.8 | 312.8 | 155.0 | — | — | — | — | — | — | — | |
| Propylene | 361.6 | — | 85.8 | — | 447.4 | 170.0 | 84.2 | — | — | — | — | — | — | — | |
| DIPE | — | — | — | 0.1 | 0.1 | — | 92.5 | 158.1 | 22.7 | 158.0 | 88.3 | 69.3 | 92.4 | 63.1 | |
| IPA | — | — | — | 1.4 | 1.4 | — | — | 86.5 | 18.7 | 77.4 | 17.4 | 9.7 | 7.7 | 35.1 | 34.2 |
| Oligomer | — | — | — | 0.0 | 0.0 | — | — | 3.7 | 6.4 | 0.9 | 6.4 | 3.6 | 2.8 | 3.7 | 2.1 |
| Water | — | 182.5 | — | 40.8 | 223.3 | — | — | 45.8 | 52.1 | 0.0 | 11.3 | 6.3 | 5.0 | 5.0 | 0.6 | zeolite Beta as catalyst shifts toward ether(s) and away from alcohol(s).

The aqueous mixture of alcohol and ether produced in the olefin conversion unit containing unconverted olefin and any inert gaseous material such as saturated hydrocarbon which may have been part of the olefin feed stream, and the small quantities of oligomer which are typically present in the reaction effluent, are then passed to a separator unit to provide a gaseous phase containing the unconverted olefin and a liquid phase containing alcohol, ether, water and oligomer. The gaseous phase is recycled to the olefin conversion unit with part of it being vented off as may be necessary to avoid build-up of any inert component(s) in the system. The aqueous phase made up of alcohol, ether and oligomer is then introduced into distillation tower to provide an azeotropic overheads fraction containing most of the ether, a minor part of the alcohol and most of the water and oligomer and a bottoms fraction containing a major part of the alcohol, a minor part of the ether and oligomer and essentially no water. Part or all of the bottoms fraction can be recycled to the olefin conversion unit to maintain a high level of alcohol therein as this has been found to shift selectivity to ether. Alternatively, part or all of the bottoms fraction can be recombined with product ether to provide a dry alcohol/ether mixture of just about any desired composition.

The distillation unit is supplied with part or all of the ether-rich upper phase recovered from a downstream decanter unit in order to reduce the water content of the final ether product even further. If all of the decanter overhead is totally recycled, the water content in the product ether will be zero. If only part of the decanter overhead is recycled, the water content in the product ether will generally be between zero and about 1 wt. %.

What is claimed is:

1. A process for producing ether containing at most relatively minor amounts of water which comprises:
   (a) contacting at least one light olefin with water in an olefin conversion unit in the presence of an acidic zeolite as catalyst to provide an aqueous mixture of alcohol and ether, the olefin conversion unit being operated under conditions which are effective to provide alcohol by the reaction of olefin and water therein and ether by the dehydration of alcohol and/or by the reaction of olefin and alcohol therein;
   (b) introducing the aqueous mixture of alcohol and ether into a distillation unit supplied with at least a part of the ether layer recovered from a downstream decantation operation, said distillation unit being operated under conditions which are effective to provide an azeotropic overheads fraction comprising ether, water, oligomer and minor amounts of alcohol, and a bottoms fraction comprising a major amount of alcohol and a minor amount of ether;
   (c) introducing the azeotropic overheads fraction into a decanter unit operated under conditions which are effective to provide an ether layer containing at most negligible amounts of water and an aqueous product containing negligible amounts of alcohol; and,
   (d) introducing at least part of the ether layer into the distillation unit to reduce the water content of the final ether product.

2. The process of claim 1 wherein the zeolite possesses a Constraint Index of no greater than about 2.

3. The process of claim 1 wherein the zeolite is selected from the group consisting of zeolite Beta, X, L, Y, REY, Deal Y, ZSM-3, ZSM-4, ZSM-12, ZSM-20 and ZSM-50.

4. The process of claim 1 wherein the zeolite is composited with a binder.

5. The process of claim 1 wherein the zeolite is composited with a binder selected from the group consisting of alumina and silica.

6. The process of claim 1 wherein the light olefin is at least one member of the group consisting of ethylene, propylene, butenes, pentenes, hexenes and heptenes.

7. The process of claim 1 wherein the olefin conversion unit is maintained under conditions comprising a temperature of from ambient to about 300° C., an overall system pressure of at least about 5 atm, a water to total olefin mole ratio of from about 0.1 to about 30 and an LHSV of from about 0.1 to about 10.

8. The process of claim 1 wherein the zeolite is zeolite Beta and the water to total olefin mole ratio is less than about 1.

9. The process of claim 1 wherein effluent from the olefin conversion unit containing unconverted olefin and, optionally, inert gaseous hydrocarbon, is introduced into a separator unit operated under conditions which are effective to provide a gaseous fraction containing unconverted olefin and a liquid fraction containing water, alcohol, ether and oligomer, the unconverted olefin being introduced to the olefin conversion unit and the liquid fraction being introduced into the distillation unit.

10. The process of claim 1 wherein part or all of the bottoms fraction from the distillation unit is introduced into the olefin conversion unit.

11. The process of claim 1 wherein part or all of the bottom fraction from the distillation unit is combined with the product ether to provide an alcohol/ether mixture.

12. The process of claim 1 wherein the olefin is propylene or propylene in admixture with propane and the product is diisopropyl ether containing less than about 3 weight percent of water.

13. The process of claim 1 wherein the aqueous layer from the decanter unit is introduced into the olefin conversion unit.

* * * * *

UNITED STATES PATENT AND TRADEMARK OFFICE
CERTIFICATE OF CORRECTION

PATENT NO. : 4,857,664

DATED : August 15, 1989

INVENTOR(S) : Tracy J. Huang, Rene B. LaPierre, Michael B. Carroll and Samuel A. Tabak It is certified that error appears in the above-identified patent and that said Letters Patent is hereby corrected as shown below:

Title page, item [75] Inventors:, add --Michael B. Carroll--.

Cols. 5 and 6, Table, numbers in row for DIPE, beginning w/col. 7, should be shifted one column to the right.

Signed and Sealed this

Seventeenth Day of March, 1992

Attest:

HARRY F. MANBECK, JR.

Attesting Officer

Commissioner of Patents and Trademarks